(12) United States Patent
Packham et al.

(10) Patent No.: US 10,716,698 B2
(45) Date of Patent: Jul. 21, 2020

(54) ADJUSTABLE COMPRESSION DEVICE

(71) Applicants: John Richard Packham, Perth (AU); Edward Joseph Khoury, Bateman (AU)

(72) Inventors: John Richard Packham, Perth (AU); Edward Joseph Khoury, Bateman (AU)

( * ) Notice: Subject to any disclaimer, the term of this patent is extended or adjusted under 35 U.S.C. 154(b) by 171 days.

(21) Appl. No.: 15/756,444

(22) PCT Filed: Aug. 26, 2016

(86) PCT No.: PCT/AU2016/050793
§ 371 (c)(1),
(2) Date: Feb. 28, 2018

(87) PCT Pub. No.: WO2017/035576
PCT Pub. Date: Mar. 9, 2017

(65) Prior Publication Data
US 2018/0243123 A1 Aug. 30, 2018

(30) Foreign Application Priority Data
Aug. 28, 2015 (AU) ................................ 2015903492

(51) Int. Cl.
*A61F 5/41* (2006.01)
*A61H 19/00* (2006.01)
(52) U.S. Cl.
CPC .............. *A61F 5/41* (2013.01); *A61H 19/32* (2013.01); *A61F 2005/414* (2013.01); *A61F 2005/417* (2013.01)

(58) Field of Classification Search
CPC ................................ A61F 5/41; A61F 2/0054
USPC ........................................................ 600/38–41
See application file for complete search history.

(56) References Cited

U.S. PATENT DOCUMENTS

| 3,147,754 A * | 9/1964 | Koessler | A61F 2/0054 |
| | | | 128/885 |
| 5,415,179 A * | 5/1995 | Mendoza | A61F 2/0054 |
| | | | 128/842 |
| 5,421,324 A * | 6/1995 | Kelly | A61F 5/41 |
| | | | 128/842 |
| 6,131,576 A * | 10/2000 | Davis | A61B 17/122 |
| | | | 128/885 |

* cited by examiner

*Primary Examiner* — Samuel G Gilbert
(74) *Attorney, Agent, or Firm* — Tope-McKay & Associates (57) ABSTRACT

An adjustable compression device (10) including an elongate rigid band (12) provided to extend around a portion of the circumference of a penis (16) is described. The band (12) includes first and second side portions (18, 20) connecting by an intermediate portion (22). An engagement member (14) is secured between the first and second side portions (18, 20) such that the engagement member (14) is rotatable about a rotational axis (24) extending between the side portions (18, 20). The engagement member (14) is off-centred relative to said rotational axis (24) such that an area defined between the engagement member (14) and the band (12) can be increased or decreased by rotation of the engagement member (14) thereby adjusting pressure applied to the penis (16).

20 Claims, 8 Drawing Sheets

ADJUSTABLE COMPRESSION DEVICE

FIELD OF THE INVENTION

The present invention relates to a device to provide compression to the penis in order to control blood flow.

BACKGROUND TO THE INVENTION

A range of treatment options are available for assisting with impotence and for controlling erections. These options include pharmaceuticals and physical devices aimed at providing a degree of control over the blood flow to and from the penis.

Physical devices available generally comprise a tourniquet type device placed around the base of the penis to restrict blood flow from the penis and thereby assist with maintaining an erection. Such devices often comprise simply an elasticised band that can be stretched and placed around the penis The present invention relates to such a device for controlling blood flow which comprises an improved construction to allow easy adjustment of the pressure applied.

SUMMARY OF THE INVENTION

According to one aspect of the present invention there is provided an adjustable compression device comprising:
an elongate rigid band provided to extend around a portion of the circumference of a penis, the band including first and second side portions connecting by an intermediate portion; and
an engagement member secured between the first and second side portions such that the engagement member is rotatable about a rotational axis extending between the side portions;
wherein the engagement member is off-centred relative to said rotational axis such that an area defined between the engagement member and the band can be increased or decreased by rotation of the engagement member thereby adjusting pressure applied to the penis.

Preferably the engagement member comprises a cylinder having its central longitudinal axis located parallel to, but offset from, the rotational axis.

Preferably the cylinder is oval shaped in longitudinal cross section, such that the cylinder comprises an oval first end wall located adjacent the first side portion, an oval second end wall located adjacent the second side portion and a cylindrical side wall extending between the first and second end surfaces.

In a preferred embodiment, an outer surface of the side wall includes an arcuate groove extending around the periphery thereof centrally between the first and second end walls.

Preferably the band comprises a U-shaped member.

Preferably a locking mechanism is provided such that the engagement member can be fixed from further rotation at one of a plurality of rotational positions.

In a preferred embodiment, the locking mechanism is releasable by compressing distal end portions of the first and second side portions of the band towards each other.

In one embodiment, the first and second side portions of the band are each provided with shaft portions extending inwardly towards each other to be received in corresponding first and second openings provided in the first and second end walls of the engagement member respectively.

In one embodiment, the locking mechanism comprises spring biased cogs provided adjacent inner surfaces of the end walls of the engagement member, the cogs including teeth provided to engage with teeth on the inner surface of the end walls, and wherein compression of the end portions of the side portions of the band moves the cogs inwardly such that the teeth disengage and the engagement member is free to rotate.

Preferably each of the cogs is spring biased by a spring provided between the cog and an internal dividing wall within the engagement member.

In one embodiment, apertures are provided passing through the shaft portions and securing screws pass through the shaft portions to engage with the cogs.

Preferably caps are provided to be inserted into the apertures from the outer sides of the first and second side portions of the band.

In one embodiment, the locking mechanism includes a releasable one-way rotation mechanism such that rotation of the engagement member towards a fully closed position is allowed and rotation in the opposite direction is prevented.

In a preferred embodiment, the engagement member is provided with a vibration device.

In one embodiment, the vibration device comprises a motor unit located within an internal cavity provided within the engagement member.

In one embodiment, the engagement member includes a first side and a second side, wherein the first side comprises a cam surface such that as the first side moves through between the band in a first direction, the area defined between engagement member and the band decreases.

BRIEF DESCRIPTION OF THE DRAWINGS

The invention will now be described, by way of example, with reference to the following drawings, in which:

FIG. 1b is a second upper perspective view of the adjustable compression device of FIG. 1a;

DETAILED DESCRIPTION OF PREFERRED EMBODIMENTS

Referring to the Figures, there is shown an adjustable compression device 10 comprising generally a rigid band 12 and an engagement member 14. The rigid band 12 comprises a relatively flat elongate member provided to extend around a portion of the circumference of a penis 16.

The band 12 comprises a rigid element formed of a suitable material, such as a plastics based material. The band 12 is formed as a U-shaped member 13 such that the band 12 comprises a planar first side portion 18, a planar second side portion 20 and an arcuate intermediate portion 22. The first and second side portions 18 and 20 are parallel to each other.

Figure 7A:
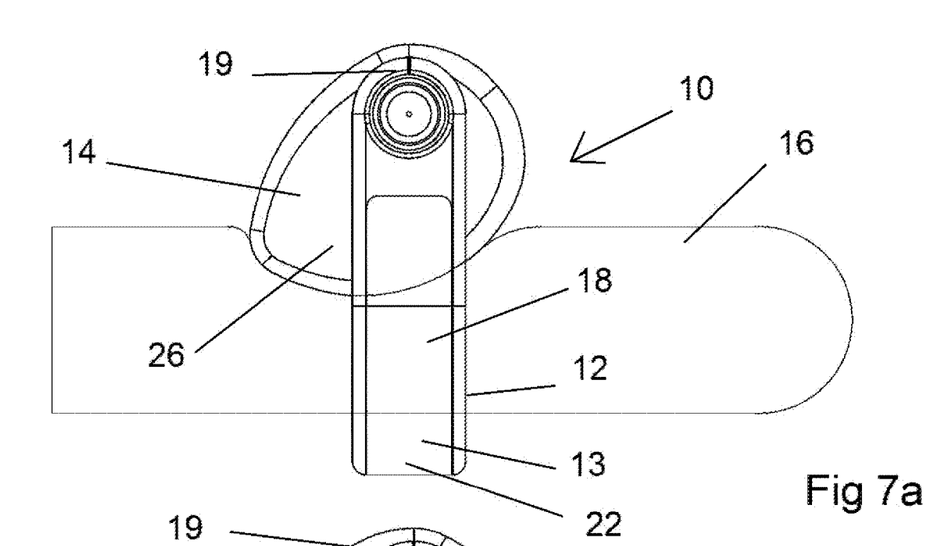
FIG. 7a is a side view of the adjustable compression device engaged with a penis with the engagement member on an upper side of the penis adjacent the base of the penis.
Figure 7B:
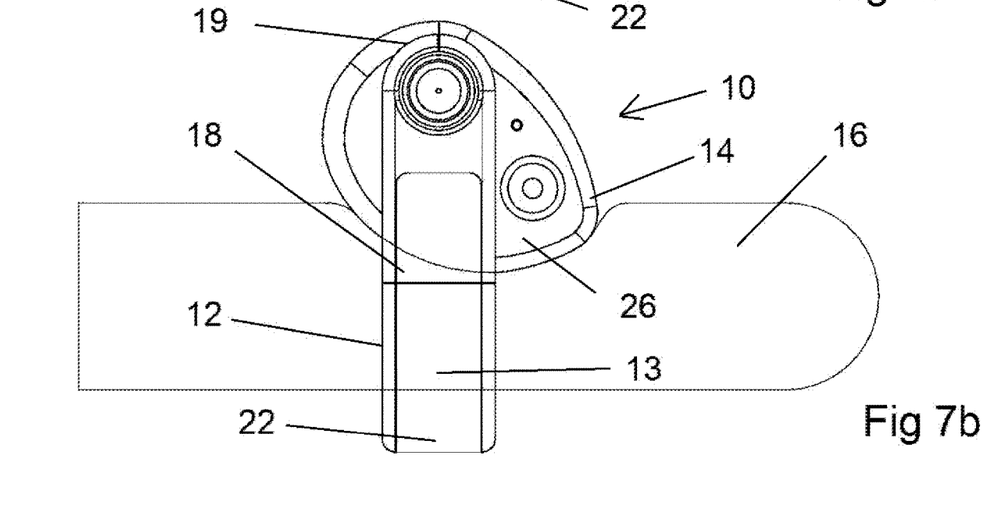
FIG. 7b is a side view of the adjustable compression device engaged with a penis with the engagement member on the upper side of the penis remote from the base of the penis.
Figure 8A:
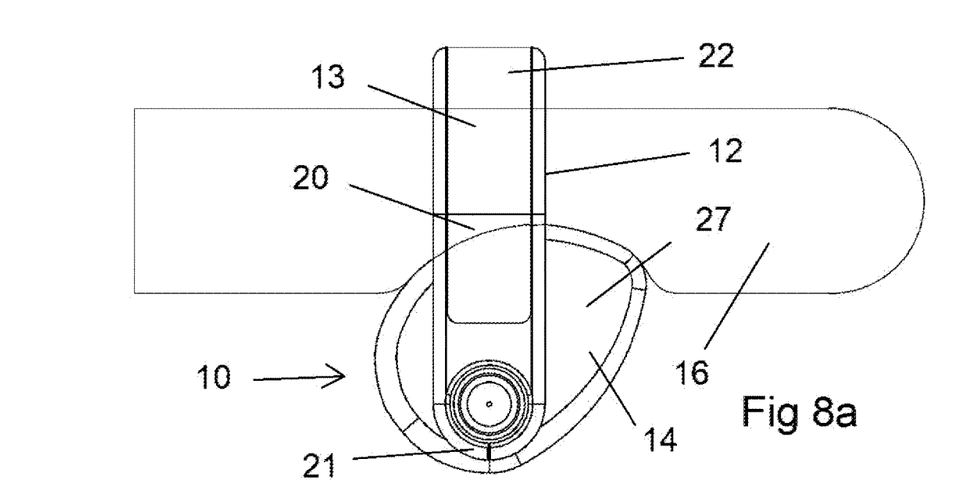
FIG. 8a is a side view of the adjustable compression device engaged with a penis with the engagement member on the lower side of the penis remote from the base of the penis.
Figure 8B:
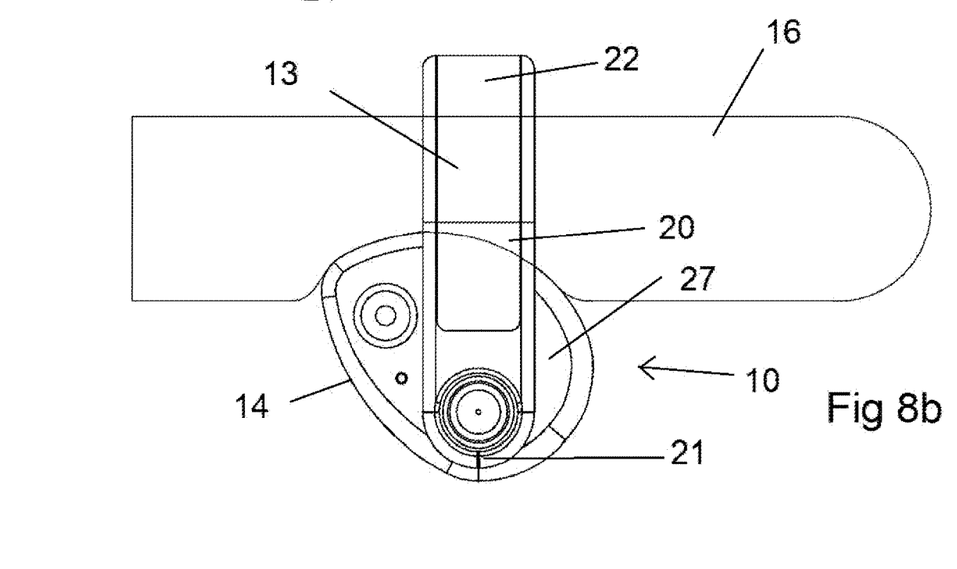
FIG. 8b is a side view of the adjustable compression device engaged with a penis with the engagement member on the lower side of the penis adjacent the base of the penis.

The U-shaped member 13 is dimensioned such that it can be received about the penis 16 as shown in FIGS. 7 and 8. In the case in which the penis 16 is received downwardly into the U-shaped member 13 (as shown in FIG. 7), distal end portions 19 and 21 of the first and second side portions 18 and 20 are located on opposed horizontal sides of the penis 16 above the penis 16. In the case in which the penis 16 is received upwardly into the U-shaped member 13 (as shown in FIG. 8), the distal end portions 19 and 21 of the first and second side portions 18 and 20 are located on opposed horizontal sides of the penis 16 below the penis 16.

The engagement member 14 is secured between the first and second side portions 18 and 20 of the U-shaped member 13 such that the engagement member 14 is rotatable relative to the U-shaped member 13. The engagement member 14 is rotatable about a rotational axis 24 extending between the distal end portions 19 and 21 of the U-shaped member 13. The engagement member 14 is also off-centred relative to the rotational axis 24 such that an area defined between the engagement member 14 and the band 12 can be increased or decreased by rotation of the engagement member 14 about the rotational axis 24.

In the embodiment shown, the engagement member 14 comprises a cylinder 15 including first and second end walls 26 and 27 connected by a cylindrical side wall 39. The side wall 39 of the cylinder 15 is generally oval in a cross section taken transverse to its longitudinal axis and the first and second end walls 26 and 27 are oval in shape. A central longitudinal axis of the cylinder 15 is located parallel to, but offset from, the rotational axis 24.

The first and second side portions 18 and 20 of the band 12 are each provided with shaft portions 30a and 30b extending inwardly towards each other. The shaft portion 30a provided on the first side portion 18 is received in a first opening 32a provided in the first end wall 26 of the engagement member 14. The shaft portion 30b provided on the second side portion 20 is received in a second opening 32b provided in the second end wall 27 of the engagement member 14. The engagement member 14 thereby rotates about the shaft portions 30a and 30b with the rotational axis 24 extending through each of the shaft portions 30a and 30b.

Figure 1A:
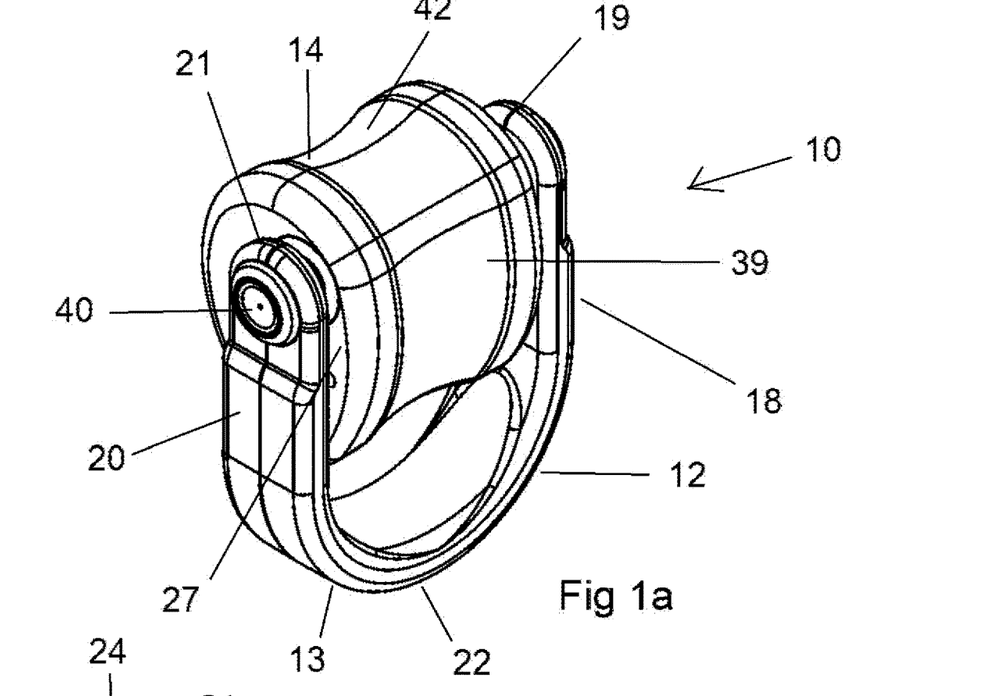
FIG. 1a is a first upper perspective view of an adjustable compression device in accordance with the present invention.
Figure 1B:
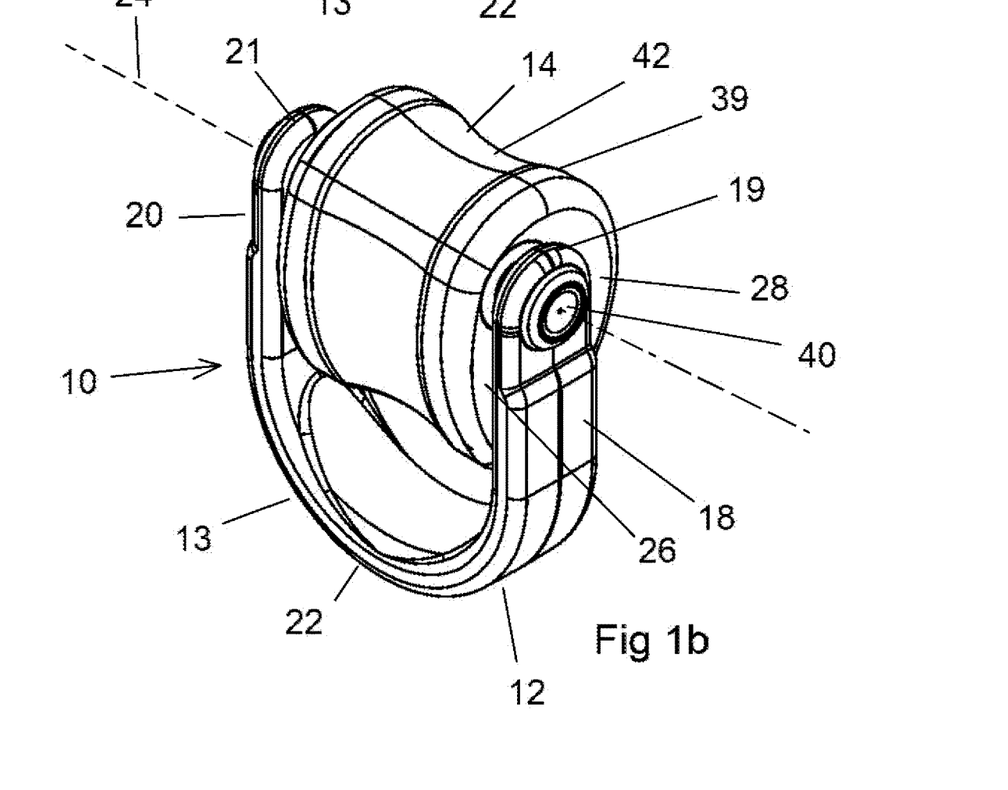
Figure 2A:
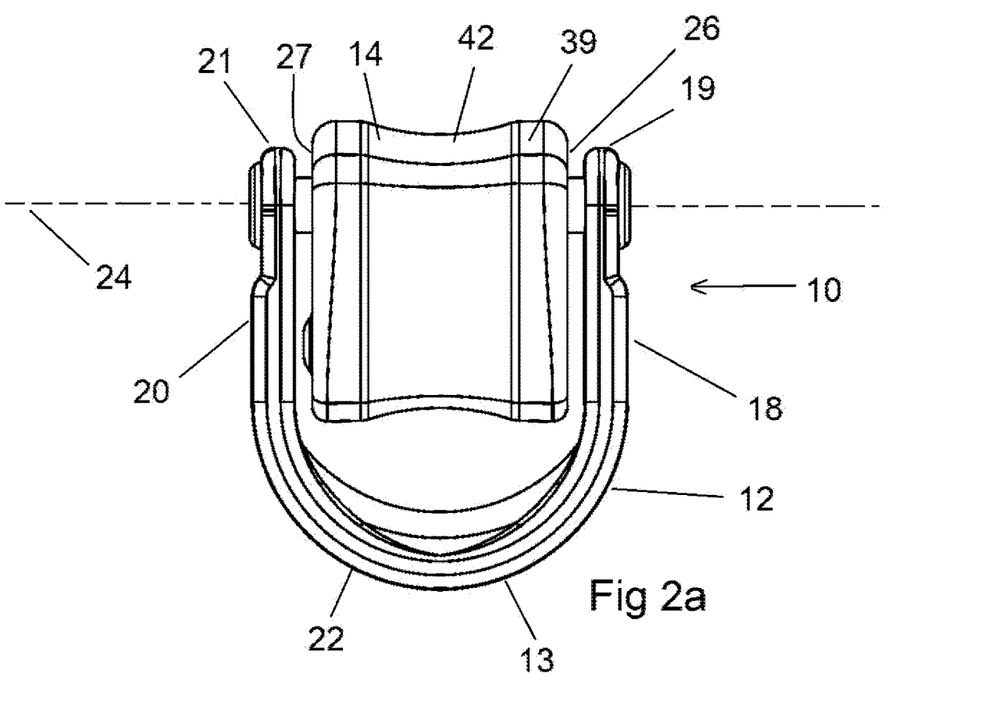
FIG. 2a is a front view of the adjustable compression device of FIG. 1.
Figure 2B:
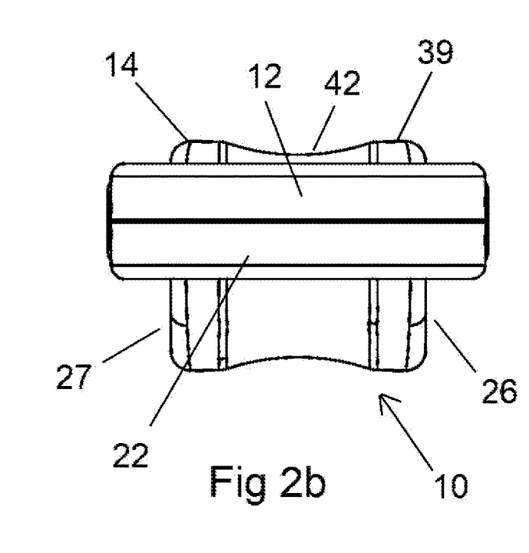
FIG. 2b is a bottom view of the adjustable compression device of FIG. 1.
Figure 2C:
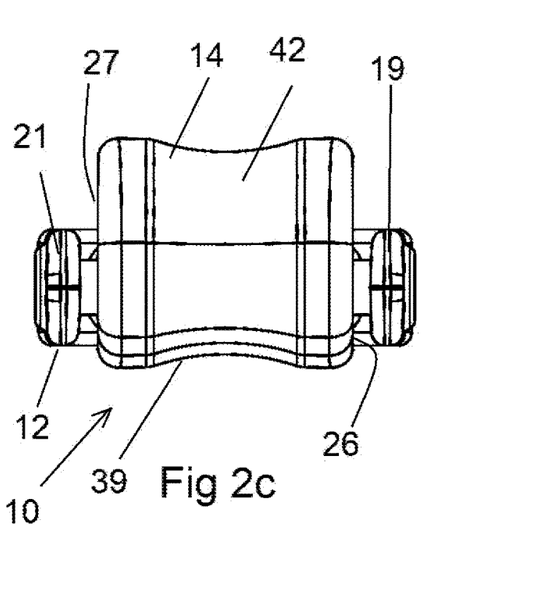
FIG. 2c is a top view of the adjustable compression device of FIG. 1.

The engagement member 14 is rotatable between a plurality of positions, in which the area defined between the engagement member 14 and the band 12 is varied. In a fully closed position, axes extending along the end walls 26 and 27 between centres of the openings 32a and 32b and the central longitudinal axis of the engagement member 14 are adjacent and parallel to the first and second side portions 18 and 20 (as shown for example in FIG. 1).

The engagement member 14 is provided with a locking mechanism provided such that the engagement member 14 can be fixed from further rotation at one of a plurality of rotational positions.

The locking mechanism includes cogs 34 provided adjacent inner surfaces of the end walls 26 and 27. The cogs 34 are provided adjacent the openings 32a and 32b such that the cogs 34 are secured to the inner ends of the shaft portions 30a and 30b. The cogs 34 include teeth 36a on a circular end face located adjacent the inner surface of the end walls 26 and 27. Further teeth 36b are provided on the inner surfaces of the end walls 26 and 27 around the openings 32a and 32b.

In the embodiment shown, apertures 28a and 28b are provided passing through the shaft portions 30a and 30b and securing screws 29 pass through the shaft portions 30a and 30b to engage with the cogs 34. Caps 40 are provided to be inserted into the apertures 28a and 28b from outer sides of the first and second side portions 18 and 20 of the band 12.

Each of the cogs 34 is spring biased to be moved towards the inner surface of the adjacent end wall 26 or 27 such that the teeth 36a on the cogs 34 engage into the teeth 36b on the end walls 26 and 27. In the embodiment shown, the cylinder 15 is provided with an inner dividing wall 52 between the first and second end walls 26 and 27 and the spring bias is provided by springs 38 located between the cogs 34 and the dividing wall 52.

Figure 6A:
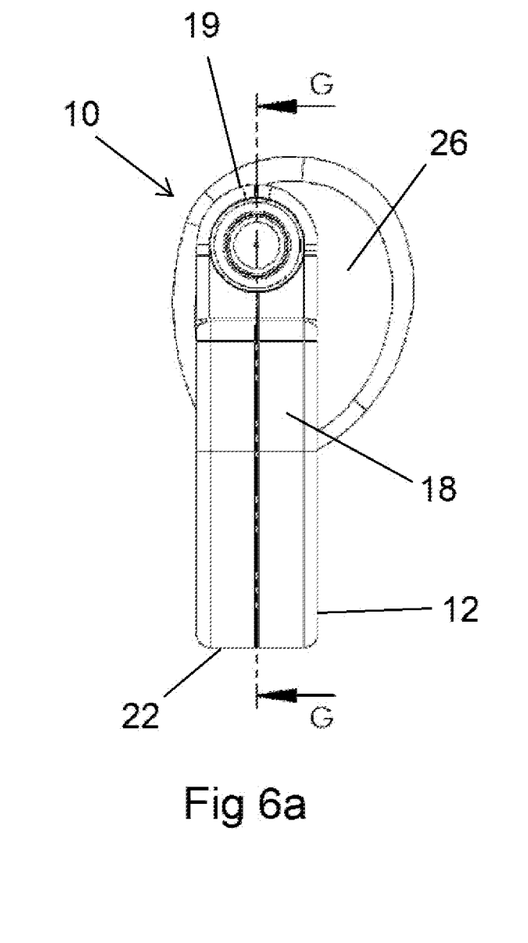
FIG. 6a is a side view of the adjustable compression device of FIG. 1 in an unlocked position.
Figure 6B:
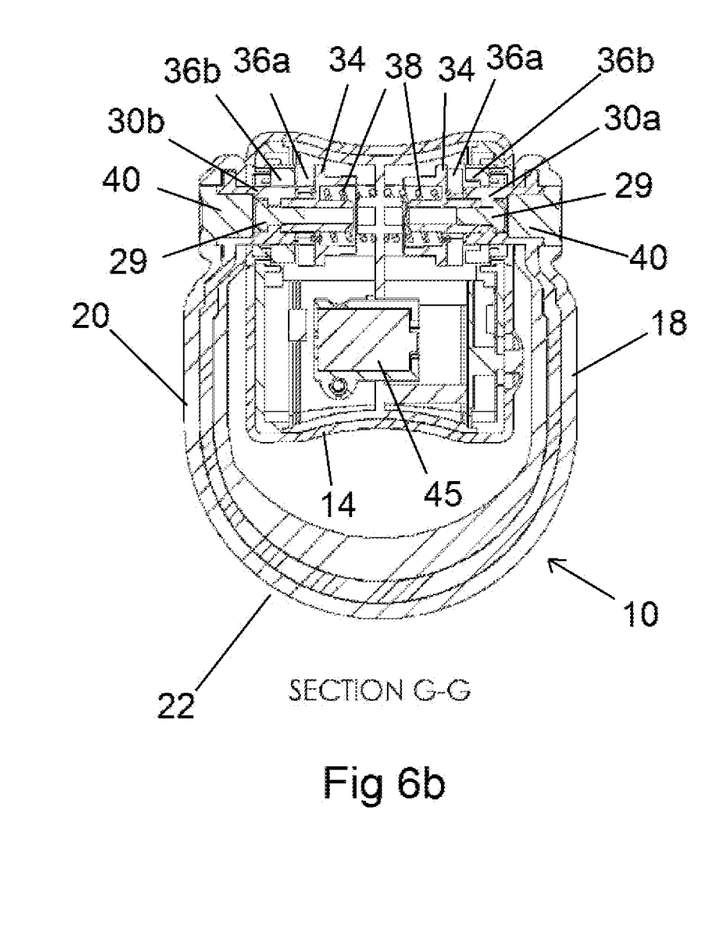
FIG. 6b is a cross sectional view of the adjustable compression device of FIG. 6a through the line G-G.

The first and second side portions 18 and 20 of the band 12 are flexible such that the distal end portions 19 and 21 thereof can be moved towards each other by compressing the distal end portions 19 and 21 towards each other. As can be seen in FIG. 6, pressing together at the caps 40 moves the shaft portions 30a and 30b towards each other, which in turn moves the cogs 34 inwardly away from the inner surfaces of the end walls 26 and 27. The teeth 36a on the cogs 34 move away from the teeth 36b on the end walls 26 and 27 and the engagement member 14 is then free to rotate relative to the band 12. On release, the springs 38 move the cogs 34 back into engagement with the teeth 36b to again lock the engagement member 14.

The locking mechanism may include a releasable one-way rotation mechanism such the engagement member 14 may rotated towards the fully closed position without disengagement of the locking mechanism but cannot be rotated away from the fully closed position without disengagement of the locking mechanism. The one-way rotation mechanism may comprise triangular shaped faces on the teeth 36a and 36b such that rotation of the engagement member 14 toward the fully closed position is allowed by relative movement of angled surfaces of the teeth 36a and 36b.

The side wall 39 of the engagement member 14 also includes a groove 42 in the outer surface thereof. The groove 42 is arcuate in shape and extends around the periphery of the side wall 39 centrally between the first and second end walls 26 and 27. The groove 42 is shaped to generally match the curvature of the surface of the penis 16 where the engagement member 14 contacts the penis 16.

Figure 3A:
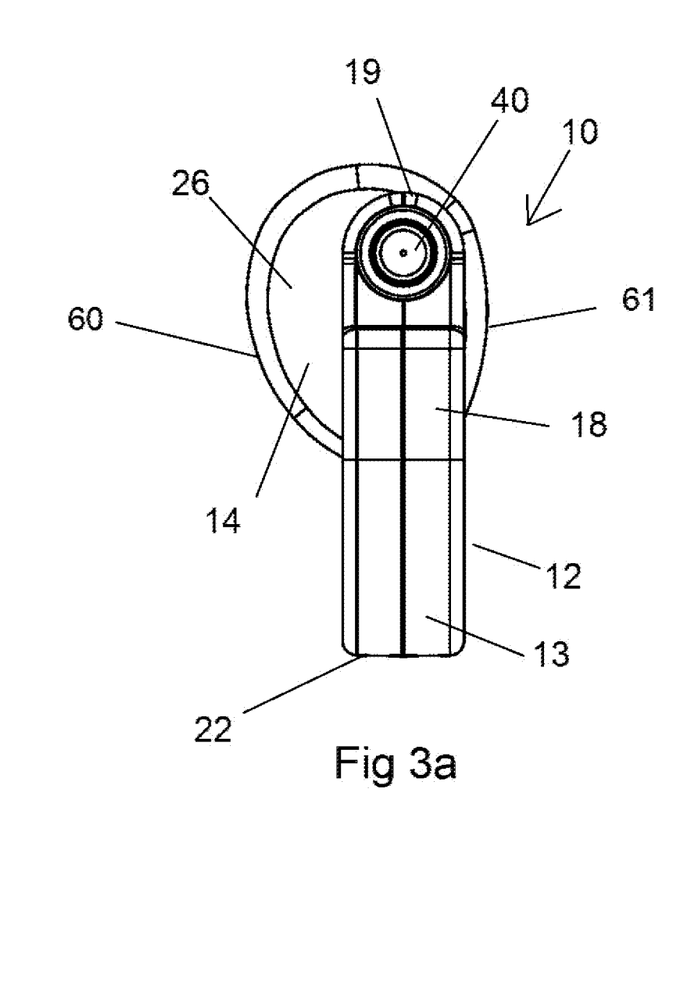
FIG. 3a is a first side view of the adjustable compression device of FIG. 1.
Figure 3B:
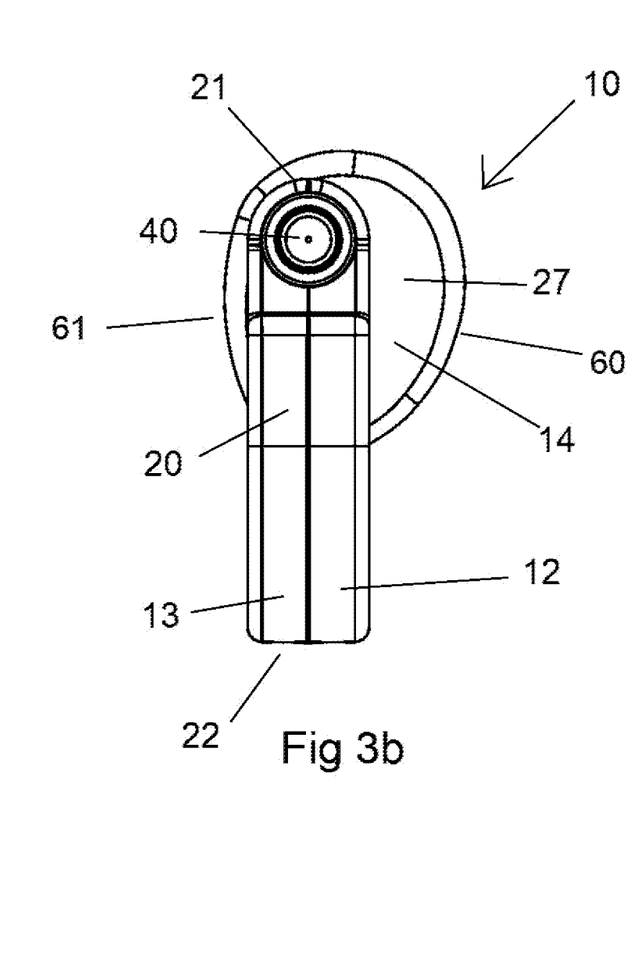
FIG. 3b is a second side view of the adjustable compression device of FIG. 1.
Figure 4:
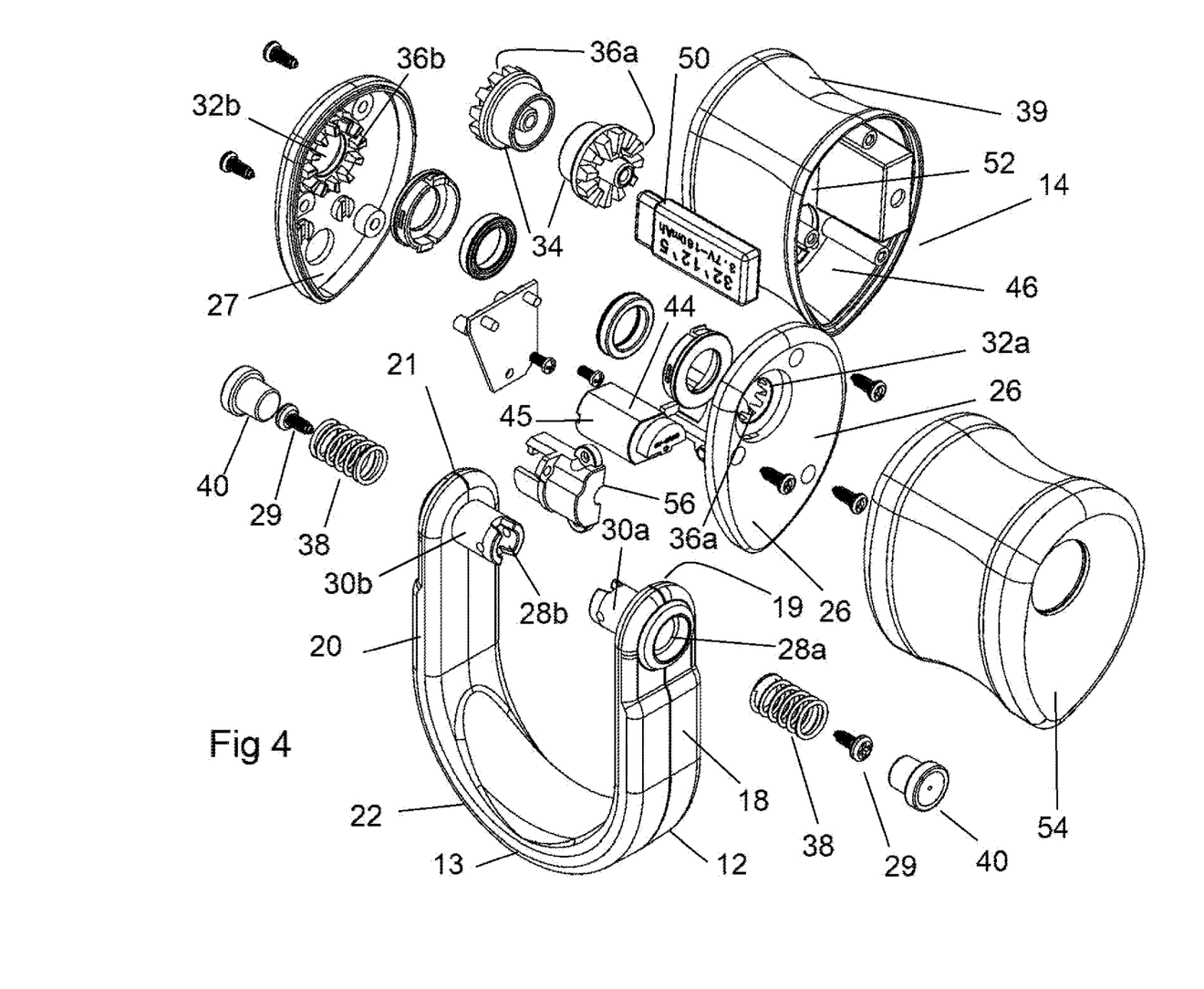
FIG. 4 is an exploded view of the adjustable compression device of FIG. 1.
Figure 5A:
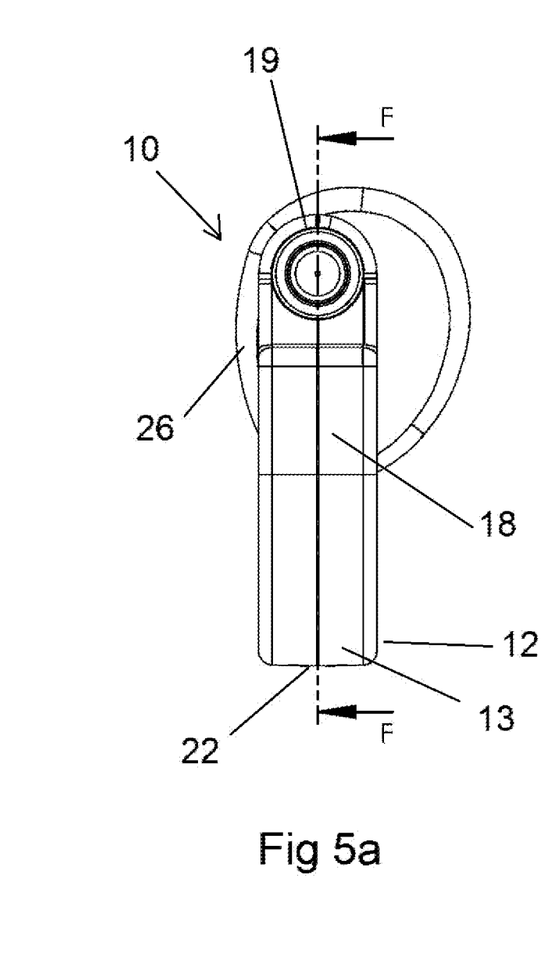
FIG. 5a is a side view of the adjustable compression device of FIG. 1 in a locked position.
Figure 5B:
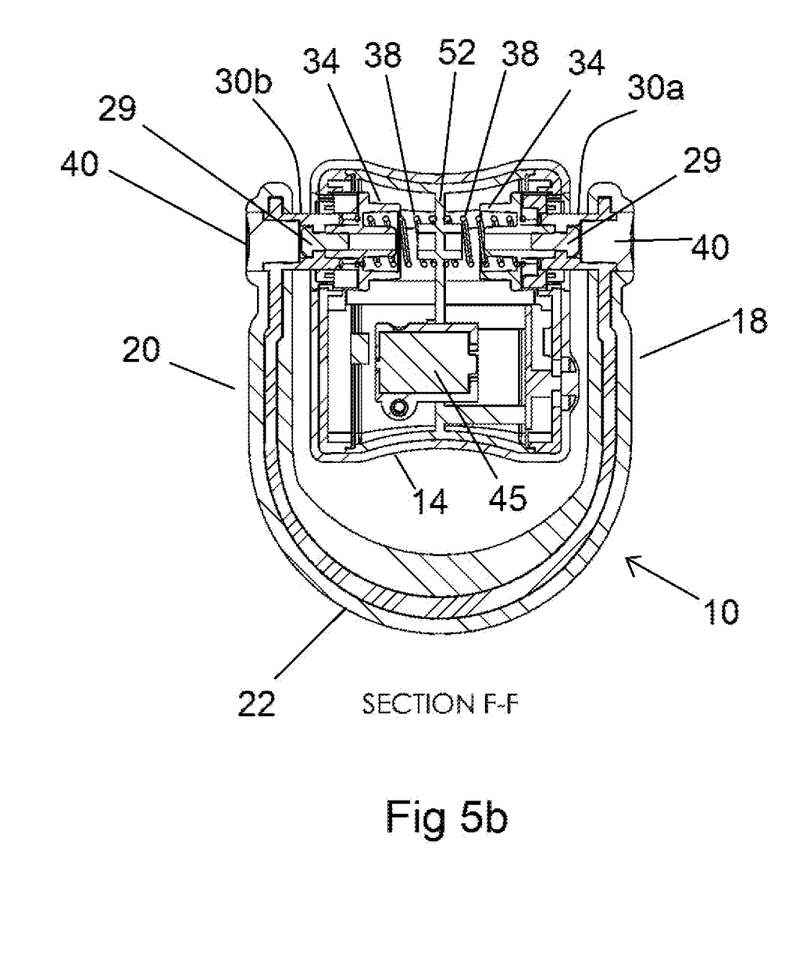
FIG. 5b is a cross sectional view of the adjustable compression device of FIG. 5a through the line F-F.

In the embodiment shown, the engagement member 14 includes a first side 60 having a different curvature from a second side 61. The side wall 39 of the engagement member 14 on the first side 60 has a greater curvature than on the second side 61, as can be seen in FIG. 3. The first side 60 of the cylinder 15 is to be used to engage the surface of the penis 16 in use. The first side 60 comprises a cam surface such as the first side 60 moves through between the band 12 in a first direction, the area defined between engagement member 14 and the band 12 decreases and as the first side 60 moves through between the band 12 in a second direction, the area defined between the engagement member 14 and the band 12 increases. That is, the radial distance between the rotational axis 24 and the side wall 39 of the engagement member 14 increases from a first end of the first side 60 to an opposite second end of the first side 60.

The second side 61 is relatively flat in comparison to the first side 60. The second side 61 may also be used to engage the penis 16, thereby providing additional flexibility in adjusting the degree of pressure applied by the engagement member 14 to the penis 16.

The engagement member 14 is provided also with a cover 54. The cover 54 extends around the end walls 26 and 27 and the side wall 39 of the engagement member 14 and is formed of a flexible resilient material for additional comfort.

The engagement member 14 is also provided with a vibration device 44. The vibration device is located within an internal cavity 46 provided within the engagement member 14. In the embodiment shown, the vibration device 44 comprises a motor unit 45 powered by a suitable power supply, such as a battery 50. The motor unit 45 in the embodiment shown is mounted through an opening in the dividing wall 52 within a motor housing 56. The vibration device 44 may be operated to vibrate the engagement member 14 in order to provide increased pleasure to both the wearer of the adjustable compression device 10 and their partner in use.

In use, the adjustable compression device 10 can be used by inserting the penis 16 between the band 12 and the engagement member 14 with the engagement member 14 located either above or below the penis 16. The engagement member 14 is rotated progressively towards the fully closed position to provide increasing pressure against the penis 16 to restrict blood flow and thereby assist in maintaining an erection. The adjustable compression device 10 may also be used with an initially flaccid penis. With the ability of the device to regulate blood flow via varying the pressure applied, the device can effectively engorge the penis with blood and maintain the blood within the penis. The engorgement process may be facilitated by the user pushing the band once it is in place into the groin area and then progressively tightening the pressure as blood flow is encouraged and then trapped in the penis.

It will be readily apparent to persons skilled in the relevant arts that various modifications and improvements may be made to the foregoing embodiments, in addition to those already described, without departing from the basic inventive concepts of the present invention.

What is claimed is:

1. An adjustable compression device comprising:
   an elongate rigid band provided to extend around a portion of a circumference of a penis, the band including first and second side portions connecting by an intermediate portion; and
   an engagement member secured between the first and second side portions such that the engagement member is rotatable about a rotational axis extending between the side portions,
   the engagement member having a cylindrical side wall being off-centred relative to said rotational axis such that an area defined between the engagement member and the band can be increased or decreased by rotation of the engagement member thereby adjusting pressure applied to the penis;
   wherein an outer surface of the side wall includes an arcuate groove extending around a periphery thereof to follow a curvature of a surface of the penis.

2. The adjustable compression device in accordance with claim 1, wherein the engagement member comprises a cylinder having its central longitudinal axis located parallel to, but offset from, the rotational axis.

3. The adjustable compression device in accordance with claim 2, wherein the cylinder is oval shaped in longitudinal cross section, such that the cylinder comprises an oval first end wall located adjacent the first side portion, an oval second end wall located adjacent the second side portion and wherein the cylindrical side wall extends between the first and second end surfaces.

4. The adjustable compression device in accordance with claim 3, wherein the band comprises a U-shaped member.

5. The adjustable compression device in accordance with claim 1, wherein the band comprises a U-shaped member.

6. The adjustable compression device in accordance with claim 1, wherein a locking mechanism is provided such that the engagement member can be fixed from further rotation at one of a plurality of rotational positions.

7. The adjustable compression device in accordance with claim 6, wherein the locking mechanism is releasable by compressing distal end portions of the first and second side portions of the band towards each other.

8. The adjustable compression device in accordance with claim 7, wherein the first and second side portions of the band are each provided with shaft portions extending inwardly towards each other to be received in corresponding first and second openings provided in the first and second end walls of the engagement member respectively.

9. The adjustable compression device in accordance with claim 8, wherein the locking mechanism comprises spring biased cogs provided adjacent inner surfaces of the end walls of the engagement member, the cogs including teeth provided to engage with teeth on the inner surface of the end walls, and wherein compression of the end portions of the side portions of the band moves the cogs inwardly such that the teeth disengage and the engagement member is free to rotate.

10. The adjustable compression device in accordance with claim 9, wherein each of the cogs is spring biased by a spring provided between the cog and an internal dividing wall within the engagement member.

11. The adjustable compression device in accordance with claim 10, wherein apertures are provided passing through the shaft portions and securing screws pass through the shaft portions to engage with the cogs.

12. The adjustable compression device in accordance with claim 11, wherein caps are provided to be inserted into the apertures from outer sides of the first and second side portions of the band.

13. The adjustable compression device in accordance with claim 12, wherein the locking mechanism includes a releasable one-way rotation mechanism such that rotation of the engagement member towards a fully closed position is allowed and rotation in an opposite direction is prevented.

14. The adjustable compression device in accordance with claim 11, wherein the locking mechanism includes a releasable one-way rotation mechanism such that rotation of the engagement member towards a fully closed position is allowed and rotation in an opposite direction is prevented.

15. The adjustable compression device in accordance with claim 10, wherein the locking mechanism includes a releasable one-way rotation mechanism such that rotation of the engagement member towards a fully closed position is allowed and rotation in an opposite direction is prevented.

16. The adjustable compression device in accordance with claim 9, wherein the locking mechanism includes a releasable one-way rotation mechanism such that rotation of the engagement member towards a fully closed position is allowed and rotation in an opposite direction is prevented.

17. The adjustable compression device in accordance with claim 1, wherein the engagement member is provided with a vibration device.

18. The adjustable compression device in accordance with claim 17, wherein the vibration device comprises a motor unit located within an internal cavity provided within the engagement member.

19. The adjustable compression device in accordance with claim 18, wherein the engagement member includes a first side and a second side, wherein the first side comprises a cam surface such that as the first side moves through between the band in a first direction, the area defined between engagement member and the band decreases.

20. The adjustable compression device in accordance with claim 1, wherein the engagement member includes a first side and a second side, wherein the first side comprises a cam surface such that as the first side moves through between the band in a first direction, the area defined between the engagement member and the band decreases.

* * * * *